(12) United States Patent
Taguchi et al.

(10) Patent No.: US 9,499,728 B2
(45) Date of Patent: Nov. 22, 2016

(54) TWO-COMPONENT TISSUE ADHESIVE AND METHOD FOR PRODUCING SAME

(75) Inventors: Tetsushi Taguchi, Tsukuba (JP); Miyuki Matsuda, Tsukuba (JP)

(73) Assignee: National Institute for Materials Science, Ibaraki (JP)

( * ) Notice: Subject to any disclaimer, the term of this patent is extended or adjusted under 35 U.S.C. 154(b) by 93 days.

(21) Appl. No.: 13/877,880

(22) PCT Filed: Oct. 4, 2011

(86) PCT No.: PCT/JP2011/072835
§ 371 (c)(1),
(2), (4) Date: Apr. 30, 2013

(87) PCT Pub. No.: WO2012/046717
PCT Pub. Date: Apr. 12, 2012

(65) Prior Publication Data
US 2013/0220174 A1  Aug. 29, 2013

(30) Foreign Application Priority Data
Oct. 5, 2010 (JP) .................................. 2010-225368

(51) Int. Cl.
C09J 189/00 (2006.01)
C09H 7/00 (2006.01)
A61L 24/10 (2006.01)
A61K 38/00 (2006.01)

(52) U.S. Cl.
CPC ............ *C09J 189/00* (2013.01); *A61L 24/104* (2013.01)

(58) Field of Classification Search
None
See application file for complete search history.

(56) References Cited

U.S. PATENT DOCUMENTS

| | | | |
|---|---|---|---|
| 4,768,523 A * | 9/1988 | Cahalan et al. ............... | 607/116 |
| 5,211,960 A * | 5/1993 | Babior ................. | A01N 1/0231 |
| | | | 424/534 |
| 5,292,333 A * | 3/1994 | Johnson ......................... | 606/214 |
| 6,897,297 B1 * | 5/2005 | Pepinsky et al. ............. | 530/402 |
| 8,367,388 B2 * | 2/2013 | Bloom et al. .................. | 435/193 |
| 2007/0161538 A1 * | 7/2007 | Yanagisawa ............ | C11D 3/225 |
| | | | 510/475 |
| 2007/0243131 A1 * | 10/2007 | Chen et al. ................... | 424/1.11 |
| 2010/0087851 A1 * | 4/2010 | Jones et al. ................... | 606/213 |

FOREIGN PATENT DOCUMENTS

| | | |
|---|---|---|
| CA | 2628720 A1 | 5/2007 |
| EP | 0018093 A1 | 10/1980 |
| JP | 09-103479 A | 4/1997 |
| JP | 11-239609 | 9/1999 |
| JP | 2006-523113 A | 10/2006 |
| JP | 2007-182407 | 7/2007 |
| JP | 2008-073443 | 4/2008 |
| JP | 2008-284256 A | 11/2008 |
| JP | 2009-515620 A | 4/2009 |
| WO | WO 2004/087227 A1 | 10/2004 |
| WO | W02009075329 A1 | 6/2009 |
| WO | WO 2009/069727 A1 | 6/2009 |
| WO | WO 2010/026782 A1 | 3/2010 |
| WO | WO 2009153750 A3 * | 6/2010 |

OTHER PUBLICATIONS

Klick-Fischer et al. (1998) Controlling absorbency in gelatin networks: Preparation and characterization of alkylated, crosslinked gelatin, J. Appli. Polym. Sci., vol. 68, pp. 281-292.*
Search Report from corresponding European Application No. 11830649.7, pp. 1-6, Aug. 21, 2014.
Taguchi et al., "Biodegradable Adhesives Composed of Human Serum Albumin and Organic Acid-based Crosslinkers with Active Ester Groups", Journal of Bioactive and Compatible Polymers, vol. 24, pp. 546-559 (2009).
Lin et al., "Preparation and Surface Activity of Gelatin Derivative Surfactants", Colloids and Surfaces A, vol. 272, pp. 8-14 (2006).
Lin et al., "The pH-Dependent Surface Properties of Gelatin-Alkenylsuccinic Acid Anhydride Derived Surfactants", Journal of Applied Polymer Science, vol. 105, pp. 3371-3377 (2007).
Taguchi et al., "Development of Tissue Adhesives", Artificial Blood, vol. 14, No. 4, pp. 118-123 (2007).
International Search Report from corresponding PCT Application No. PCT/JP2011/072835, pp. 1-4 (Dec. 27, 2011).

* cited by examiner

*Primary Examiner* — Anand Desai
*Assistant Examiner* — Samuel Liu
(74) *Attorney, Agent, or Firm* — Hoffman & Baron, LLP

(57) ABSTRACT

The present invention addresses the problem of providing: a two-component tissue adhesive having high adhesive strength and high biocompatibility; and a method for producing the two-component tissue adhesive. The present invention involves a two-component tissue adhesive comprising hydrophobically-modified gelatin as a first agent and a cross-linking reagent as a second agent. The hydrophobically-modified gelatin is provided with an amino group and a hydrophobic group on the side chain thereof, and the cross-linking reagent has two or more active ester groups or anhydrides within a single molecule.

2 Claims, 4 Drawing Sheets

TWO-COMPONENT TISSUE ADHESIVE AND METHOD FOR PRODUCING SAME

CROSS-REFERENCE TO RELATED APPLICATIONS

This application is a U.S. National Phase Application of International Application No. PCT/JP2011/072835 filed on Oct. 4, 2011 and asserts priority to Japanese Application No. 2010-225368 filed on Oct. 5, 2010, all of which are hereby incorporated by reference in their entirety.

TECHNICAL FIELD

The present invention relates to a two-component tissue adhesive and a method for producing the same.

BACKGROUND ART

A tissue adhesive means an adhesive used for biological tissues such as blood vessels, skin, and the like (hereunder, referred to as tissue), in an operation such as cardiovascular surgery. With use of this adhesive, it is possible to prevent blood leaking and such risks so as to improve the safety of the operation.

At present, there are three major types of tissue adhesives as follows.

The first adhesive is a cyanoacrylate based tissue adhesive, such as DERMABOND as a commercial product. This adhesive has a problem in that the biocompatibility is low, although the adhesive strength is high.

The second adhesive is a biopolymer-aldehyde based tissue adhesive, such as Gelatin Resolcinol Formaldehyde (GRF glue as a commercial product. This adhesive also has a problem in that the biocompatibility is low, although the adhesive strength is high.

The third adhesive is a fibrin based tissue adhesive, such as Bolheal as a commercial product. This adhesive has an opposite problem in that the adhesive strength is low, although the biocompatibility is high.

In this way, it has been so far a problem of this technology that there is no tissue adhesive satisfying both excellent properties of the adhesive strength and the biocompatibility.

In recent years, regarding the fibrin based tissue adhesive, it has been elucidated that a tissue adhesive comprising human serum albumin (hereunder, referred to as HSA) and a cross-linking reagent has high adhesive strength (Non-Patent Document 1).

HSA is a serum protein made from blood preparations. It is a globular protein having a diameter of about 10 nm with a molecular weight of 69,000. Moreover, this is a negatively charged acidic protein. In addition, disuccinimidyl tartarate (hereunder, referred to as DST) has been used as the cross-linking reagent.

However, since any product using a blood preparation is classified as a medicinal product, considerable efforts are required for the approval and clearance. Moreover, once it is approved as a medicinal product, the usage record has to be kept continually for 20 years after the approval. This requires considerable efforts, which is a problem.

For this reason, it has been considered to use gelatin as a non-blood preparation instead of HSA. For example, Patent Document 1 has disclosed a medical material prepared by crosslinking gelatin with succinimidized poly-L-glutamic acid. Moreover, Patent Document 2 relating to a tissue adhesive film has disclosed a tissue adhesive film made from gelatin or collagen. However, they have a problem in that the adhesive strength is not enough.

In addition, Patent Document 3 relating to a tissue adhesive formulation has disclosed a tissue adhesive formulation which comprises a mixture of a synthetic and/or cross-linkable material in a particulate form and a particulate material. However, this tissue adhesive formulation also has a problem in that the adhesive strength is not enough.

Furthermore, papers relating to gelatin in which an alkyl group has been introduced on the side chain, have been reported (Non-patent documents 2 and 3).

However, solving the above-mentioned problems has yet to be achieved.

PRIOR ART DOCUMENTS

Patent Documents

Patent Document 1: Japanese Unexamined Patent Application, First Publication No. H09-103479
Patent Document 2: Japanese Unexamined Patent Application, First Publication No. 2008-284256
Patent Document 3: Published Japanese Translation of PCT International Application No. 2006-523113

Non-Patent Documents

Non-Patent Document 1: J. Bioact. Compact. Polym., 24, 546-559 (2009)
Non-Patent Document 2: Li-Huei Lin, Keng-Ming Chen, COLLOIDS AND SURFACES A, 272, 2006, 8-14
Non-Patent Document 3: Li-Huei Lin, Keng-Ming Chen, Chee-Chan Wang, Journal of Applied Polymer Science, 105, 2007, 3371-3377

DISCLOSURE OF INVENTION

Problems to be Solved by the Invention

The present invention addresses the problem of providing a two-component tissue adhesive having high adhesive strength and high biocompatibility and a method for producing the same.

Means to Solve the Problems

The inventors of the present invention and others have discovered that a two-component tissue adhesive having high adhesive strength and high biocompatibility can be provided by using hydrophobically-modified gelatin in which a hydrophobic group has been introduced in gelatin of a molecular weight of 10,000 or higher and lower than 50,000, instead of HSA. This has led to the completion of the present invention.

The present invention has the following structures.

The two-component tissue adhesive of the present invention comprises: a first agent which contains hydrophobically-modified gelatin that is provided with an amino group and a hydrophobic group on the side chain; and a second agent which contains a cross-linking reagent that has two or more active ester groups or anhydrides within a single molecule.

In the two-component tissue adhesive of the present invention, the hydrophobically-modified gelatin may be a polymer in which two or more amino acids are linearly linked and a part of Lys residues in the amino acids is substituted with the hydrophobic group.

In the two-component tissue adhesive of the present invention, the hydrophobic group may be any one type or a combination of two or more types selected from the group consisting of a cholesteryl group, an oleyl group, an isostearyl group, a stearyl group, an isopalmityl group, a myristyl group, a lauryl group, a capric group, a pelargol group, a caprylic group, a caproyl group, an α-linolenyl group, a stearidonyl group, an eicosapentaenoyl group, and a docosahexaenyl group.

In the two-component tissue adhesive of the present invention, the first agent may further contain gelatin which is any one type or a combination of two or more types selected from the group consisting of natural gelatin derived from human, porcine, bovine, or fish species, and genetically modified gelatin thereof.

In the two-component tissue adhesive of the present invention, the molecular weight of the hydrophobically-modified gelatin may be 10,000 or higher, and lower than 50,000.

In the two-component tissue adhesive of the present invention, the cross-linking reagent may be any one type or a combination of two or more types selected from the group consisting of genipin, tartaric acid, citric acid, malic acid, glutamic acid, aspartic acid, oxalacetic acid, cis-aconitic acid, 2-ketoglutaric acid, polytartaric acid, polycitric acid, polymalic acid, polyglutamic acid, and polyaspartic acid.

The method for producing a two-component tissue adhesive of the present invention comprises: a step of adding an organic molecule that has a hydrophobic group, to a solution in which gelatin has been dissolved, in the presence of an amine, so as to synthesize hydrophobically-modified gelatin by partially substituting amino groups on the side chain of the gelatin with the hydrophobic group; and a step of mixing a cross-linking reagent that has two or more active ester groups or anhydrides within a single molecule, in a solution containing the hydrophobically-modified gelatin.

Effect of the Invention

The two-component tissue adhesive of the present invention is a two-component tissue adhesive comprising a first agent which contains hydrophobically-modified gelatin and a second agent which contains a cross-linking reagent. Here, the hydrophobically-modified gelatin is provided with an amino group and a hydrophobic group on the side chain thereof, and the cross-linking reagent has two or more active ester groups or anhydrides within a single molecule. For this reason, the amino groups which constitute the hydrophobically-modified gelatin can be mutually cross-linked by the active ester groups or the acid anhydride of the cross-linking reagent. Thus, a chemically firm attachment can be created. Furthermore, a physically firm attachment with the tissue can be created by having the hydrophobic group penetrating (anchored) into the tissue. Thus, the adhesive strength can be enhanced. Furthermore, since the hydrophobically-modified gelatin is readily decomposable by an enzyme (collagenase) in the course of wound healing of a tissue, the biocompatibility can be enhanced. Accordingly, the present invention is capable of providing a tissue adhesive having high adhesive strength and high biocompatibility.

The method for producing a two-component tissue adhesive of the present invention comprises: a step of adding an organic molecule that has a hydrophobic group, to a solution in which gelatin has been dissolved, in the presence of an amine, so as to synthesize hydrophobically-modified gelatin by partially substituting amino groups on the side chain of the gelatin with the hydrophobic group, and filling the same in a first container; and a step of filling a cross-linking reagent that has two or more active ester groups or anhydrides within a single molecule, in a second container. For this reason, the tissue adhesive having high adhesive strength and high biocompatibility, as mentioned above, can be readily obtained by mixing the hydrophobically-modified gelatin in the first container and the cross-linking reagent in the second container.

EMBODIMENTS FOR CARRYING OUT THE INVENTION

Embodiments of the Present Invention

Hereunder is a description of a tissue adhesive and a method for producing the same, which are the embodiments of the present invention, with reference to the appended drawings.

Figure 1:
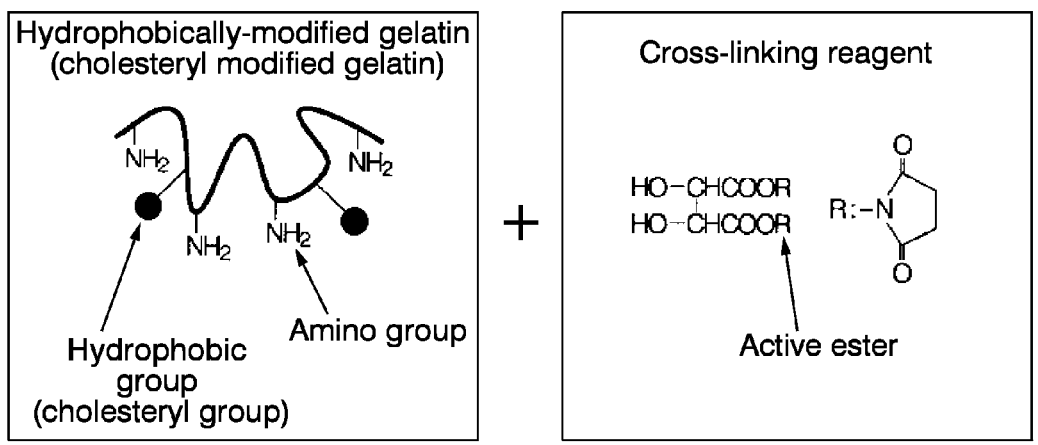
FIG. 1 is a schematic diagram illustrating an example of the structure of the tissue adhesive of the present invention.

As shown in FIG. 1, the two-component tissue adhesive serving as an embodiment of the present invention comprises a first agent which contains hydrophobically-modified gelatin and a second agent which contains a cross-linking reagent. The first agent may further contain gelatin which is any one type or a combination of two or more types selected from the group consisting of natural gelatin derived from human, porcine, bovine, or fish species, and genetically modified gelatin.

For adhering a biological tissue by using the tissue adhesive, water is necessary to cause a cross-linking reaction between the hydrophobically-modified gelatin and the cross-linking reagent. The water is preferably a buffer solution whose pH is from 6 to 8. The cross-linking reaction can be made to progress most quickly by using a buffer solution within this pH range.

The hydrophobically-modified gelatin comprises a main chain consisting of gelatin, and an amino group and the hydrophobic group on the side chain thereof. Because the gelatin structure is used, the adhesive can be readily decomposed by an enzyme. Therefore, the biocompatibility can be enhanced.

The molecular weight of the hydrophobically-modified gelatin is preferably 10,000 or higher, and lower than 50,000. The adhesive strength can be improved by setting the molecular weight of the hydrophobically-modified gelatin within this range. If the molecular weight of the hydrophobically-modified gelatin is 50,000 or higher, the self-association of the gelatin itself is so strong that the permeability into the tissue is deteriorated. Therefore, the adhesive strength is lowered. Moreover, if the molecular weight of the hydrophobically-modified gelatin is lower than 10,000, the dissolubility into water is notably lowered due to the hydrophobic modification. Therefore, it is difficult to use such gelatin as a component of the tissue adhesive.

Lys is one of the protein-constituting α-amino acids, and is an essential amino acid. It is an amino acid having an ε-amino group on the side chain. A part of the amino groups of Lys can be readily substituted with a hydrophobic group by a known method. In the hydrophobically-modified gelatin in the first agent of the present invention, a part of the Lys amino groups is substituted with a hydrophobic group.

The hydrophobic group introduced in the gelatin is anchored to the tissue at the time of the reaction with the cross-linking reagent, by which the gelatin can be firmly fixed to the tissue. By so doing, the hydrophobically-modified gelatin can be adhered to the tissue by a physically firm attachment. Therefore, the adhesive strength can be improved.

If the hydrophobic group is soluble with water, the hydrophobicity is low, which makes it difficult to stick the hydrophobic group to the tissue. Therefore, the hydrophobically-modified gelatin can not be firmly fixed to the tissue. On the other hand, if the hydrophobic group is insoluble with water, the hydrophobic property is displayed, which makes it difficult to anchor the hydrophobic group to the tissue. Therefore, it is difficult to firmly fix the hydrophobically-modified gelatin to the tissue.

The hydrophobic group can be exemplified by a cholesteryl group represented by the following formula (1), and also an oleyl group, an isostearyl group, a stearyl group, an isopalmityl group, a myristyl group, a lauryl group, a capric group, a pelargol group, a caprylic group, a caproyl group, an α-linolenyl group, a stearidonyl group, an eicosapentaenoyl group, and a docosahexaenyl group. Any one type or a combination of two or more types selected from the group consisting of these can be used.

[Formula 1]

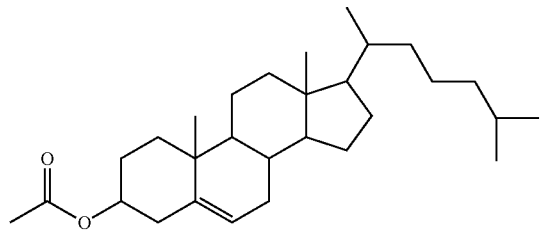

(1)

The cross-linking reagent comprises an organic molecule that has two or more active ester groups or anhydrides within a single molecule. By having two or more active ester groups or anhydrides within a single molecule, these cross-linking reagents are able to react with and bind to two amino groups of the hydrophobically-modified gelatin. Thus, a firm adhesive construct can be formed by cross-linking two or more molecules of the hydrophobically-modified gelatin.

The cross-linking reagent can be exemplified by one molecule selected from the group consisting of genipin, or tartaric acid, citric acid, malic acid, glutamic acid, aspartic acid, oxalacetic acid, cis-aconitic acid, 2-ketoglutaric acid, polytartaric acid, polycitric acid, polymalic acid, polyglutamic acid, and polyaspartic acid, wherein two or more active ester groups or acid anhydrides are held within a single molecule of the above-mentioned molecules.

The active ester group is preferably any one type or a combination of two or more types of N-hydroxysuccinimidyl or N-hydroxysulfosuccinimidyl groups. This is because succinimide is a succinic acid derivative existing in a metabolic pathway in vivo, and has been actually used for an FDA sanctioned tissue adhesive (sealant).

More specifically, the cross-linking reagent can be exemplified by disuccinimidyl tartrate represented by the following formula (2).

[Formula 2]

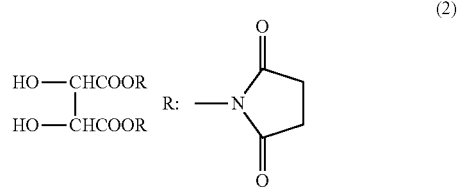

(2)

<Tissue Adhesion with Use of Two-Component Tissue Adhesive of this Embodiment>

Next is a description of the tissue adhesion with use of the two-component tissue adhesive of this embodiment.

Figure 2:
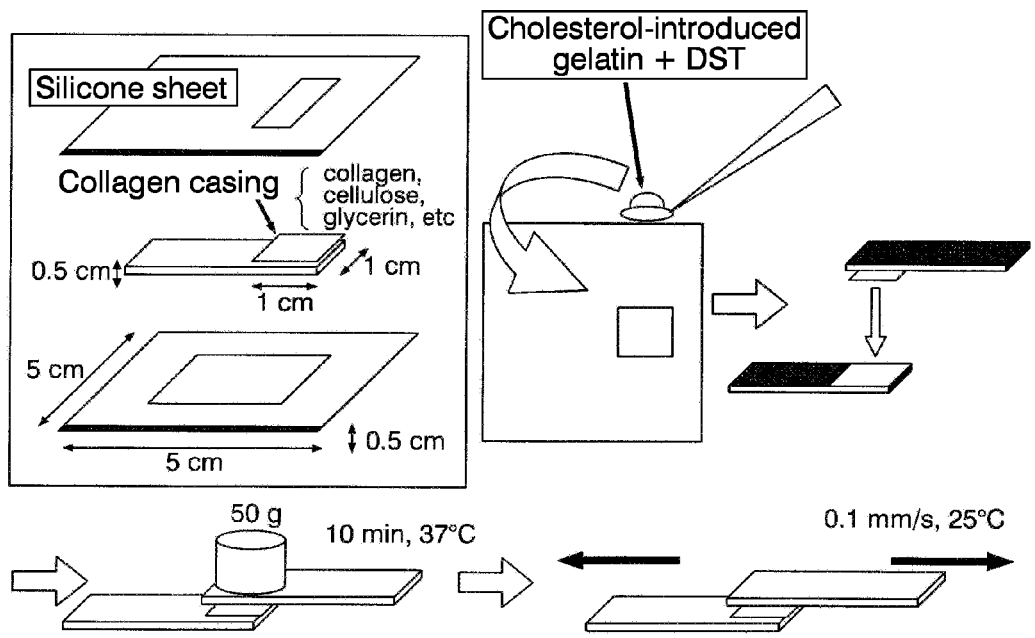
FIG. 2 is a schematic diagram illustrating an example of the adhesion method with use of the tissue adhesive of the present invention.

FIG. 2 is a process schematic diagram illustrating an example of the tissue adhesion method with use of the tissue adhesive of this embodiment.

First, as shown in the top left of FIG. 2, a tissue having an approximately rectangular shape in a planar view (for example, length 1 cm×width 1 cm, and height 0.5 cm) is formed on a part of a surface of a plastic substrate having an approximately rectangular shape in a planar view (for example, length 3 cm×width 1 cm, and height 0.5 cm). Regarding the tissue, a collagen casing composed of collagen, cellulose, glycerin, and other components is used as an imitation skin.

Next, another tissue is formed on a part of a surface of a different plastic substrate having an approximately rectangular shape in a planar view, in the same manner.

Next, an aqueous solution of the hydrophobically-modified gelatin (first agent) and the cross-linking reagent (second agent) are mixed to prepare a liquid adhesive material. Note that, the solvents for use in the first agent and the second agent of the two-component tissue adhesive of the present invention are preferably buffer solutions whose pH is from 6 to 8.

Next, as shown in the top right of FIG. 2, the liquid adhesive material is applied to the tissue on the surface of the plastic substrate.

Next, as shown in the bottom of FIG. 2, the tissue on the surface of the plastic substrate is pushed onto the liquid adhesive material on the tissue. The attached substrates are left standing while being weighted with a weight for a fixed period of time.

The leaving time is necessary for the tissue adhesive to be solidified, and is appropriately set according to the proportion of the constituent materials in the tissue adhesive. For example, the time can be set to about 10 minutes. In addition, in this case, the substrates may be heated to about 37° C., for example.

Figure 3:
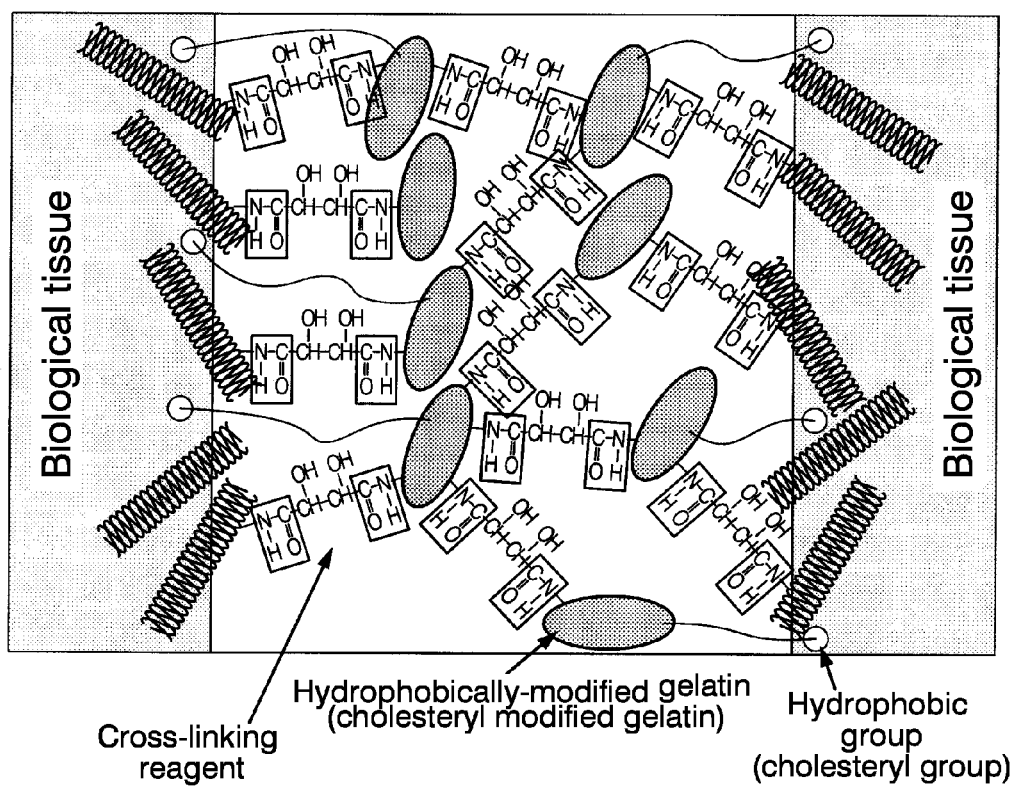
FIG. 3 is a schematic diagram illustrating an example of adhesion with use of the tissue adhesive of the present invention.

FIG. 3 is a schematic diagram illustrating an example of tissue adhesion with use of the tissue adhesive serving as an embodiment of the present invention.

As shown in FIG. 3, an amino group of the hydrophobically-modified gelatin and an active ester group of the cross-linking reagent are reacted by a hydrolysis reaction, by which an amide bond is formed. At this time, N-hydroxysuccinimide in the active ester group is separated. Moreover, another active ester group of this cross-linking reagent is reacted with an amino group of another hydrophobically-modified gelatin, a protein such as collagen, or the like, existing in the biological tissue, by which an amide bond is formed. By so doing, two molecules of the hydrophobically-modified gelatin are cross-linked by a single cross-linking reagent.

When this cross-linking reaction occurs in a chain-like manner, a construct in which a plurality of molecules of the hydrophobically-modified gelatin are firmly bound by the cross-linking reagents is formed. By so doing, this construct is made chemically firm.

In other words, it is thought that the chemical reaction represented by the following formula (3) is generated. In the formula (3), —COOR represents an active ester of the cross-linking reagent, and —NH$_2$ represents an amino group of the hydrophobically-modified gelatin.

[Formula 3]

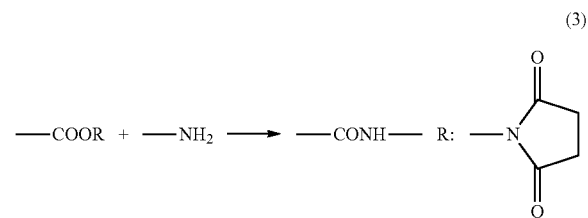

(3)

Moreover, as shown in FIG. 3, the hydrophobic groups having a fixed molecular weight and a fixed size are sticking to the tissue through hydrophobic interaction. Therefore, the hydrophobically-modified gelatin is firmly fixed to the tissue. By so doing, the construct is adhered to the surface of the tissue by a physically firm attachment.

In this embodiment, the adhesive is left standing at room temperature until it is solidified after the adhesion. However, the adhesive may be heated so as to accelerate the curing rate as long as the temperature is 37° C. or lower.

<Method for Producing Two-Component Tissue Adhesive>

Next is a description of a method for producing a two-component tissue adhesive serving as an embodiment of the present invention.

The method for producing a two-component tissue adhesive serving as an embodiment of the present invention comprises: a step of synthesizing hydrophobically-modified gelatin, and filling the same in a container, and a step of filling a cross-linking reagent in a different container.

(Step of Synthesizing and Filling Hydrophobically-Modified Gelatin)

The step of synthesizing hydrophobically-modified gelatin is a step of adding an organic molecule that has a hydrophobic group, to a solution in which gelatin has been dissolved, in the presence of an amine, so as to synthesize hydrophobically-modified gelatin by partially substituting amino groups on the side chain of the gelatin with the hydrophobic group.

The gelatin is selected so that the molecular weight would be 10,000 or higher, and lower than 50,000.

First, an acid chloride that has a hydrophobic group which is reactive with an amino group is mixed with gelatin dissolved in an organic solvent, in the presence of a triethylamine, so as to prepare a mixture solution in a container.

As the organic solvent, dimethylsulfoxide (DMSO) can be used, for example.

The organic molecule can be exemplified by cholesteryl chloroformate represented by the following formula (4).

Next, the mixture solution is heated and stirred under an inert gas atmosphere. For example, this can be done under a nitrogen atmosphere at a heating temperature of 80° C. for a stirring time of a day and a night.

[Formula 4]

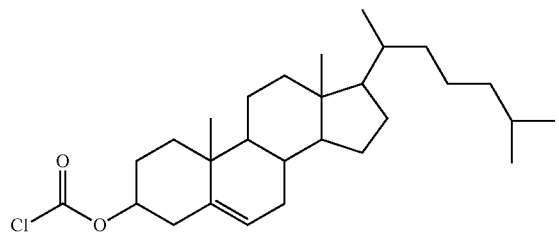

(4)

Next, this mixture solution is added dropwise to an ice cold ethanol solvent. Next, this solution is filtrated through a glass filter or the like.

Furthermore, the filtrated matter is washed with an organic solvent. By so doing, impurities in the filtrated matter can be removed so as to improve the purity of the hydrophobically-modified gelatin. Regarding this organic solvent for the washing purpose, ethanol or ethyl acetate can be used, for example.

From the above-mentioned step, hydrophobically-modified gelatin in which amino groups on the side chain of the gelatin are partially substituted with the hydrophobic group can be formed. This hydrophobically-modified gelatin is appropriately mixed with a predetermined amount of water or a buffer solution, and then filled in a container to serve as a first agent.

(Step of Filling Cross-Linking Reagent)

The step of filling a cross-linking reagent is a step of filling a cross-linking reagent that has two or more active ester groups or anhydrides within a single molecule in another container differing from that of the first agent.

From the above-mentioned step, a two-component tissue adhesive comprising the first agent which contains hydrophobically-modified gelatin and the second agent which contains the cross-linking reagent can be produced.

In the two-component tissue adhesive serving as an embodiment of the present invention, unmodified gelatin (referred to as original gelatin) can be additionally mixed in the first agent in order to adjust the proportion of the hydrophobically-modified gelatin in the tissue adhesive to an optimum value so as to much improve the adhesive strength.

In the production of the tissue adhesive, a predetermined amount of water or a buffer solution may be mixed therein after the hydrophobically-modified gelatin serving as an embodiment of the present invention has been produced. The time up to the solidification can be suitably set by appropriately setting the pH of the water or the buffer solution.

The two-component tissue adhesive serving as an embodiment of the present invention comprises a first agent which contains hydrophobically-modified gelatin and a second agent which contains a cross-linking reagent. This hydrophobically-modified gelatin is provided with an amino group and a hydrophobic group on the side chain thereof, and the cross-linking reagent has two or more active ester groups or an anhydride. For this reason, the amino groups of the hydrophobically-modified gelatin and the amino groups of proteins such as collagen or the like existing in the biological tissue can be mutually cross-linked by the active ester groups or the acid anhydride of the cross-linking reagent. Thus, a chemically firm attachment can be created. Furthermore, a physically firm attachment can also be created by having the hydrophobic group piercing (anchored) into the tissue. Therefore, the adhesive strength can be enhanced. In addition, the hydrophobically-modified gelatin can be readily decomposed by an enzyme (collagenase) in the course of wound healing. Therefore, inflammation reaction, calcification, and the like can be suppressed.

In the two-component tissue adhesive serving as an embodiment of the present invention, the structure is such that the hydrophobically-modified gelatin is a polymer in which two or more amino acids are linearly linked and a part of Lys residues in the amino acids is substituted with a hydrophobic group. For this reason, the amino groups existing in the hydrophobically-modified gelatin can be mutually cross-linked by the active ester groups of the cross-linking reagent. Therefore, a chemically firm attachment can be created, by which the adhesive strength can be enhanced. In addition, the hydrophobically-modified gelatin can be readily decomposed by an enzyme (collagenase) in the course of wound healing, by which the biocompatibility can be enhanced.

In the two-component tissue adhesive serving as an embodiment of the present invention, the structure is such that the hydrophobic group is any one type or a combination of two or more types selected from the group consisting of a cholesteryl group, an oleyl group, an isostearyl group, a stearyl group, an isopalmityl group, a myristyl group, a lauryl group, a capric group, a pelargol group, a caprylic group, a caproyl group, an α-linolenyl group, a stearidonyl group, an eicosapentaenoyl group, and a docosahexaenyl group. For this reason, a physically firm attachment can be created by having the hydrophobic group piercing (anchored) into the tissue, by which the adhesive strength can be enhanced.

In the two-component tissue adhesive serving as an embodiment of the present invention, the structure is such that gelatin which is any one type or a combination of two or more types selected from the group consisting of natural gelatin derived from human, porcine, bovine, or fish species, or genetically modified gelatin thereof, is included. For this reason, the attachment of the tissue adhesive can be made chemically firm.

In the two-component tissue adhesive serving as an embodiment of the present invention, the structure is such that the molecular weight of the hydrophobically-modified gelatin is 10,000 or higher, and lower than 50,000. For this reason, the attachment of the tissue adhesive can be made chemically firm.

In the two-component tissue adhesive serving as an embodiment of the present invention, the structure is such that the cross-linking reagent is any one type or a combination of two or more types selected from the group consisting of genipin, tartaric acid, citric acid, malic acid, glutamic acid, aspartic acid, oxalacetic acid, cis-aconitic acid, 2-ketoglutaric acid, polytartaric acid, polycitric acid, polymalic acid, polyglutamic acid, and polyaspartic acid, wherein two or more active ester groups or acid anhydrides are held within a single molecule of the above-mentioned molecules. For this reason, the amino groups of the hydrophobically-modified gelatin and the amino groups of proteins such as collagen or the like existing in the biological tissue can be mutually cross-linked by the active ester groups or the acid anhydride of the cross-linking reagent. Therefore, the attachment of the tissue adhesive can be made chemically firm.

The method for producing a two-component tissue adhesive serving as an embodiment of the present invention comprises: a step of adding an organic molecule that has a hydrophobic group, to a solution in which gelatin has been dissolved, in the presence of a triethylamine, so as to synthesize hydrophobically-modified gelatin by partially substituting amino groups on the side chain of the gelatin with the hydrophobic group, and filling the same in a first container; and a step of filling a cross-linking reagent that has two or more active ester groups or anhydrides within a single molecule, in a second container. For this reason, a tissue adhesive having high adhesive strength and high biocompatibility can be readily produced.

The two-component tissue adhesive and the method for producing the same serving as the embodiments of the present invention are not to be limited to the above-mentioned embodiments, and various modifications can be made and executed within the scope of the technical idea of the present invention. Specific examples of these embodiments are shown in the following Examples. However, the present invention is not to be limited to these Examples.

EXAMPLES

Example 1

Synthesis of Hydrophobically-Modified Gelatin (Cholesteryl Groups-Modified Gelatin First, 300 g of gelatin was dissolved by stirring in 2.97 L of DMSO, and kept at 80° C. Next, 0.03 L of triethylamine was added thereto.

Next, cholesteryl chloroformate was added at 10% with respect to the amino groups of the gelatin, and dissolved by stiffing at 80° C. The mixture was allowed to react by stiffing under a nitrogen atmosphere for a day and a night.

Next, the obtained crude cholesteryl groups-modified gelatin solution was added dropwise to 9 L of ice cold ethanol so as to stop the reaction. The reaction product was precipitated, and then was filtrated through a glass filter. This was further washed with 3 L of ethanol three more times. Furthermore, the residue was again washed with 3 L of ethyl acetate three times, and then freeze-dried. By so doing, a white solid matter (cholesteryl group-modified gelatin) was obtained.

(Mixing with Cross-Linking Reagents: Preparation of Tissue Adhesive)

Solutions in which the obtained hydrophobically-modified gelatin (having a molecular weight of 20,000) and the original gelatin (having a molecular weight of 20,000) had been mixed at various proportions were prepared using 0.1M-phosphate buffer solution (pH 6.0). 200 µL of the obtained solution was mixed with DST serving as cross-linking reagents so that the mole ratio of succinimidyl group/amino group would be 1. Thereafter, the mixture was stirred for 5 seconds. By so doing, the tissue adhesive was prepared.

In Example 1, the preparation was conducted so that the percent by mass of the cholesteryl groups-modified gelatin in the tissue adhesive would be 10 (wt %) (final concentration of 70 wt %).

When the molecular weight was 20,000 and the cholesterol introduction rate was 10%, the yield was 250.3 g and the yield rate was 82%. The adhesive strength of the tissue adhesive of Example 1 was 58.2 kPa.

The introduction of the cholesteryl group was confirmed by proton nuclear magnetic resonance ($^1$H-NMR), which showed the peak of C18 proton around 0.67 ppm.

(Evaluation of Adhesive Strength of Tissue Adhesive)

First, two plastic plates (length of 3 cm, width of 1 cm, and thickness of 0.5 mm), onto which collagen casings were pasted so as to cover about one third (1 cm×1 cm) of the whole area of one surface, were prepared.

Next, the tissue adhesive of Example 1 was applied to the surface of the collagen casing pasted onto one of the plastic plates. Note that the application was done immediately after dispersing DST in the phosphate buffer solution having been mixed with the obtained hydrophobically-modified gelatin and the original gelatin at various proportions.

Next, the surface of the collagen casing pasted onto the other plastic plate was pushed thereon, and these plates were left standing while a weight of 50 g was placed thereon at 37° C. for 10 minutes.

Next, the tensile test of these two plastic plates was performed by applying tensile strengths in mutually opposite directions parallel to the plane of the plastic substrates at a speed of 0.1 mm/s and an environmental temperature of 25° C., using a known tensile testing machine (Texture Analyzer TA.XTplus (EIKO Instruments)).

By so doing, the adhesive strength (average) of the tissue adhesive of Example 1 having been prepared so that the percent by mass of the cholesteryl groups-modified gelatin in the tissue adhesive would be 0 (wt %) (final concentration of 70 wt %) was shown to be 57.1 kPa. The adhesive strength (average) means the average value of the first to third times. The first time means an individually measured result of an adhesive in a certain condition. The second time shows the strength of an adhesive having been individually prepared in the same condition as that of the first time. The third time shows the strength of an adhesive having been individually prepared in the same condition as those of the first and second times.

(Evaluation of Biocompatibility of Tissue Adhesive (1))

The cured products of the tissue adhesive having various compositions were molded to have a diameter of 8 mm and a thickness of 1 mm. The degradability in the subcutaneous area and the inflammation of the surrounding tissue in the back of the rats were evaluated in a time course manner for 3 to 28 days.

The GRF glue (Nippon BXI Inc.) was used as a Comparative Example.

(Evaluation of Biocompatibility of Tissue Adhesive (2))

The cured products of the tissue adhesive having various compositions were molded to have a diameter of 5 mm and a thickness of 1 mm. These products were implanted subcutaneously in the back of transgenic mice (20 weeks old, BALB/C-Tg (NFκB-RE-luc)-Xen) modified to have a luciferase activity in the promoter region of the receptor of a transcription factor involved with inflammation. After 7 days, the degree of inflammation was evaluated by measuring the luminescence intensity (photon/sec) of the luminescence after 15 minutes from the abdominal administration of 300 µL of luciferin, using the IVIS Lumina II (a product of Xenogen). The average value of the cured products of the tissue adhesive implanted in three mice was adopted as the luminescence intensity. The GRF glue (Nippon BXI Inc.) was used as a Comparative Example.

Example 2

The tissue adhesive of Example 2 was produced in the same manner as that of Example 1, except that the preparation was conducted so that the percent by mass of the cholesteryl group-modified gelatin in the tissue adhesive would be 20 (wt %) (final concentration of 70 wt %).

The adhesive strength of the tissue adhesive of Example 2 was 61.5 kPa. Moreover, after 14 days, the degradability and absorptivity were observed, meaning that the biocompatibility was seen.

Example 3

The tissue adhesive of Example 3 was produced in the same manner as that of Example 1, except that the preparation was conducted so that the percent by mass of the cholesteryl group-modified gelatin in the tissue adhesive would be 30 (wt %) (final concentration of 70 wt %).

The adhesive strength of the tissue adhesive of Example 3 was 58.6 kPa.

Example 4

The tissue adhesive of Example 4 was produced in the same manner as that of Example 1, except that the preparation was conducted so that the percent by mass of the cholesteryl group-modified gelatin in the tissue adhesive would be 50 (wt %) (final concentration of 70 wt %).

The adhesive strength of the tissue adhesive of Example 4 was 62.0 kPa.

Example 5

The tissue adhesive of Example 5 was produced in the same manner as that of Example 1, except that the preparation was conducted so that the percent by mass of the cholesteryl group-modified gelatin in the tissue adhesive would be 70 (wt %) (final concentration of 70 wt %).

The adhesive strength of the tissue adhesive of Example 5 was 68.5 kPa.

Moreover, after 14 days, the degradability and absorptivity were observed, meaning that the biocompatibility was seen. In addition, the luminescence intensity of NFκB-RE using the transgenic mice of Example 5 was 300.77 (×10$^6$ photon/sec), meaning that the biocompatibility was seen.

Example 6

The tissue adhesive of Example 6 was produced in the same manner as that of Example 1, except that the preparation was conducted so that the percent by mass of the cholesteryl group-modified gelatin in the tissue adhesive would be 100 (wt %) (final concentration of 70 wt %).

The adhesive strength of the tissue adhesive of Example 6 was 54.7 kPa.

Example 7

The tissue adhesive of Example 7 was produced in the same manner as that of Example 1, except that the preparation was conducted so that the percent by mass of the cholesteryl group-modified gelatin in the tissue adhesive would be 10 (wt %) (final concentration of 70 wt %), and the mole ratio of succinimidyl group/amino group would be 2.

The adhesive strength of the tissue adhesive of Example 7 was 62.0 kPa.

Example 8

The tissue adhesive of Example 8 was produced in the same manner as that of Example 1, except that the preparation was conducted so that the percent by mass of the cholesteryl group-modified gelatin in the tissue adhesive would be 20 (wt %) (final concentration of 70 wt %), and the mole ratio of succinimidyl group/amino group would be 2.

The adhesive strength of the tissue adhesive of Example 10 was 75.0 kPa. In addition, the luminescence intensity of NFκB-RE using the transgenic mice of Example 10 was 282.17 ($\times 10^6$ photon/sec), meaning that the biocompatibility was seen.

Example 9

The tissue adhesive of Example 9 was produced in the same manner as that of Example 1, except that the preparation was conducted so that the percent by mass of the cholesteryl group-modified gelatin in the tissue adhesive would be 30 (wt %) (final concentration of 70 wt %), and the mole ratio of succinimidyl group/amino group would be 2.

The adhesive strength of the tissue adhesive of Example 9 was 51.1 kPa.

Example 10

The tissue adhesive of Example 10 was produced in the same manner as that of Example 1, except that the preparation was conducted so that the percent by mass of the cholesteryl group-modified gelatin in the tissue adhesive would be 50 (wt %) (final concentration of 70 wt %), and the mole ratio of succinimidyl group/amino group would be 2.

The adhesive strength of the tissue adhesive of Example 10 was 63.0 kPa.

Example 11

The tissue adhesive of Example 11 was produced in the same manner as that of Example 1, except that the preparation was conducted so that the percent by mass of the cholesteryl group-modified gelatin in the tissue adhesive would be 70 (wt %) (final concentration of 70 wt %), and the mole ratio of succinimidyl group/amino group would be 2.

The adhesive strength of the tissue adhesive of Example 11 was 58.9 kPa.

Example 12

The tissue adhesive of Example 12 was produced in the same manner as that of Example 1, except that the preparation was conducted so that the percent by mass of the cholesteryl group-modified gelatin in the tissue adhesive would be 100 (wt %) (final concentration of 70 wt %), and the mole ratio of succinimidyl group/amino group would be 2.

The adhesive strength of the tissue adhesive of Example 12 was 55.9 kPa.

Example 13

The tissue adhesive of Example 13 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 10 (wt %) (final concentration of 60 wt %), and the mole ratio of succinimidyl group/amino group would be 0.2.

When the molecular weight was 50,000 and the cholesterol introduction rate was 10%, the yield was 252.2 g and the yield rate was 81%. The introduction of the cholesteryl group was confirmed by proton nuclear magnetic resonance ($^1$H-NMR), which showed the peak of C18 proton around 0.67 ppm.

The adhesive strength of the tissue adhesive of Example 13 after 10 minutes was 11.6 kPa.

Example 14

The tissue adhesive of Example 14 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 10 (wt %) (final concentration of 60 wt %), and the mole ratio of succinimidyl group/amino group would be 0.5.

The adhesive strength of the tissue adhesive of Example 14 after 10 minutes was 12.2 kPa.

Example 15

The tissue adhesive of Example 15 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 10 (wt %) (final concentration of 60 wt %), and the mole ratio of succinimidyl group/amino group would be 1.

The adhesive strength of the tissue adhesive of Example 15 after 10 minutes was 13.9 kPa.

Example 16

The tissue adhesive of Example 16 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 10 (wt %) (final concentration of 60 wt %), and the mole ratio of succinimidyl group/amino group would be 2.

The adhesive strength of the tissue adhesive of Example 16 after 10 minutes was 5.5 kPa.

Example 17

The tissue adhesive of Example 17 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 10 (wt %) (final concentration of 70 wt %), and the mole ratio of succinimidyl group/amino group would be 0.2.

The adhesive strength of the tissue adhesive of Example 17 after 10 minutes was 17.1 kPa.

Example 18

The tissue adhesive of Example 18 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 10 (wt %) (final concentration of 70 wt %), and the mole ratio of succinimidyl group/amino group would be 0.5.

The adhesive strength of the tissue adhesive of Example 18 after 10 minutes was 30.1 kPa.

Example 19

The tissue adhesive of Example 19 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 10 (wt %) (final concentration of 70 wt %), and the mole ratio of succinimidyl group/amino group would be 1.

The adhesive strength of the tissue adhesive of Example 19 after 10 minutes was 22.8 kPa.

Example 20

The tissue adhesive of Example 20 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 20 (wt %) (final concentration of 70 wt %), and the mole ratio of succinimidyl group/amino group would be 1.

The adhesive strength of the tissue adhesive of Example 20 after 10 minutes was 28.6 kPa.

Example 21

The tissue adhesive of Example 21 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 30 (wt %) (final concentration of 70 wt %), and the mole ratio of succinimidyl group/amino group would be 1.

The adhesive strength of the tissue adhesive of Example 21 after 10 minutes was 24.1 kPa.

Example 22

The tissue adhesive of Example 22 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 50 (wt %) (final concentration of 70 wt %), and the mole ratio of succinimidyl group/amino group would be 1.

The adhesive strength of the tissue adhesive of Example 22 after 10 minutes was 18.9 kPa.

Example 23

The tissue adhesive of Example 23 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 70 (wt %) (final concentration of 70 wt %), and the mole ratio of succinimidyl group/amino group would be 1.

The adhesive strength of the tissue adhesive of Example 23 after 10 minutes was 24.3 kPa.

Example 24

The tissue adhesive of Example 24 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 100 (wt %) (final concentration of 70 wt %), and the mole ratio of succinimidyl group/amino group would be 1.

The adhesive strength of the tissue adhesive of Example 24 after 10 minutes was 26.9 kPa.

Example 25

The tissue adhesive of Example 25 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 10 (wt %) (final concentration of 70 wt %), and the mole ratio of succinimidyl group/amino group would be 2.

The adhesive strength of the tissue adhesive of Example 25 after 15 minutes was 19.5 kPa.

Moreover, after 7 days, the degradability and absorptivity were observed, meaning that the biocompatibility was seen.

Example 26

The tissue adhesive of Example 26 was produced in the same manner as that of Example 1, except that the preparation was done with use of gelatin and cholesteryl group-modified gelatin having molecular weights of 50,000 so that the percent by mass of the cholesteryl group-modified gelatin in the tissue adhesive would be 80 (wt %) (final concentration of 70 wt %), and the mole ratio of succinimidyl group/amino group would be 2.

The adhesive strength of the tissue adhesive of Example 26 after 15 minutes was 25.9 kPa.

Moreover, after 7 days, the degradability and absorptivity were observed, meaning that the biocompatibility was seen.

Example 27

The tissue adhesive of Example 27 was produced in the same manner as that of Example 1, except that the preparation was conducted so that the percent by mass of the cholesteryl group-modified gelatin in the tissue adhesive would be 80 (wt %) (final concentration of 80 wt %), and the mole ratio of succinimidyl group/amino group would be 2.

The adhesive strength of the tissue adhesive of Example 27 was 76.2 kPa. However, the viscosity was higher than that of the final concentration of 70 wt %, meaning the handling property was inferior.

Comparative Example 1

The adhesive strength and the biocompatibility of Comparative Example 1 were evaluated in the same manner as that of Example 1, except for that a commercial product of aldehyde based adhesive, GRF glue (Nippon BXI Inc.), was used.

The adhesive strength of the tissue adhesive of Comparative Example 1 was 41.2 kPa.

Moreover, even after 14 days, the degradability and absorptivity were not observed, meaning that the biocompatibility was low. In addition, the luminescence intensity of NFκB-RE using the transgenic mice of Comparative Example 1 was 516.30 (×10$^6$ photon/sec), meaning that the inflammation-inducibility was seen as compared to the Examples.

Comparative Example 2

The cholesteryl group-modified gelatin having a molecular weight of 2,000 was also synthesized in the same manner. However, the viscosity of the solution was too low to have enough adhesive strength.

Table 1 is a summary of the conditions and the adhesive strengths of Examples 1 to 6.

TABLE 1

| | Succinimidyl group:Amino group = 1:1 Molecular weight of 20,000, Gelatin concentration of 70% | | | |
|---|---|---|---|---|
| 10% chol Gelatin | Adhesive strength (kPa) | | | |
| content (wt %) | First time | Second time | Third time | Average |
| Example 1 | 10 | 61.6 | 58.8 | 54 | 58.2 |
| Example 2 | 20 | 46.2 | 84.9 | 53.5 | 61.5 |
| Example 3 | 30 | 62.3 | 55.5 | 57.9 | 58.6 |
| Example 4 | 50 | 62.2 | 58.6 | 65.3 | 62 |
| Example 5 | 70 | 68 | 69.5 | 68.1 | 68.5 |
| Example 6 | 100 | 44.8 | 56.9 | 62.4 | 54.7 |

Table 2 is a summary of the conditions and the adhesive strengths of Examples 7 to 12.

TABLE 2

| | Succinimidyl group:Amino group = 2:1 Molecular weight of 20,000, Gelatin concentration of 70% | | | |
|---|---|---|---|---|
| 10% chol Gelatin | Adhesive strength (kPa) | | | |
| content (wt %) | First time | Second time | Third time | Average |
| Example 7 | 10 | 55 | 64.5 | 66.7 | 62 |
| Example 8 | 20 | 68.4 | 86.4 | 70 | 75 |
| Example 9 | 30 | 57.1 | 47.7 | 48.4 | 51.1 |
| Example 10 | 50 | 64.7 | 54.4 | 70 | 63 |
| Example 11 | 70 | 71.2 | 51.9 | 53.6 | 58.9 |
| Example 12 | 100 | 56.8 | 57 | 53.9 | 55.9 |

Table 3 is a summary of the conditions and the adhesive strengths of Examples 13 to 16.

TABLE 3

| | 10% chol Gelatin content (10 wt %) Molecular weight of 50,000, Gelatin concentration of 60% | |
|---|---|---|
| | Succinimidyl group:Amino group | Adhesive strength (kPa) |
| Example 13 | 0.2:1 | 11.6 |
| Example 14 | 0.5:1 | 12.2 |
| Example 15 | 1:1 | 13.9 |
| Example 16 | 2:1 | 5.5 |

Table 4 is a summary of the conditions and the adhesive strengths of Examples 17 and 18.

TABLE 4

| | 10% chol Gelatin content (10 wt %) Molecular weight of 50,000, Gelatin concentration of 70% | |
|---|---|---|
| | Succinimidyl group:Amino group | Adhesive strength (kPa) |
| Example 17 | 0.2:1 | 17.1 |
| Example 18 | 0.5:1 | 30.1 |

Table 5 is a summary of the conditions and the adhesive strengths of Examples 19 to 24.

TABLE 5

| | Succinimidyl group:Amino group = 1:1 Molecular weight of 50,000, Gelatin concentration of 70% | |
|---|---|---|
| | 10% chol Gelatin content (wt %) | Adhesive strength (kPa) |
| Example 19 | 10 | 22.8 |
| Example 20 | 20 | 28.6 |
| Example 21 | 30 | 24.1 |
| Example 22 | 50 | 18.9 |
| Example 23 | 70 | 24.3 |
| Example 24 | 100 | 26.9 |

Table 6 is a summary of the conditions and the adhesive strengths of Examples 25 and 26.

TABLE 6

| | Succinimidyl group:Amino group = 2:1 Molecular weight of 50,000, Gelatin concentration of 70% | |
|---|---|---|
| | 10% chol Gelatin content (wt %) | Adhesive strength (kPa) |
| Example 25 | 10 | 19.5 |
| Example 26 | 80 | 25.9 |

Table 7 is a summary of the condition and the adhesive strength of Example 27.

TABLE 7

| | Succinimidyl group:Amino group = 2:1 Molecular weight of 20,000, Gelatin concentration of 80% | |
|---|---|---|
| | 10% chol Gelatin content (wt %) | Adhesive strength (kPa) |
| Example 27 | 80 | 76.2 |

Table 8 is a summary of the condition and the adhesive strength of Comparative Example 1.

TABLE 8

| | | Adhesive strength (kPa) | | | |
|---|---|---|---|---|---|
| | | First time | Second time | Third time | Average |
| Comparative Example 1 | GRF glue | 46.3 | 42.9 | 34.5 | 41.2 |

Table 9 and Table 10 are summaries of the results of the biocompatibility.

TABLE 9

| | | Conditions | | | Biocompatibility (degradability) | | | |
|---|---|---|---|---|---|---|---|---|
| | Mw | Conc. (%) | 10% chol Gelatin content (wt %) | Succinimidyl group:Amino group | Day 1 | Day 3 | Day 7 | Day 14 |
| Example 2 | 20,000 | 70 | 20 | 1:1 | Not Good | Not Good | — | Good |
| Example 5 | 20,000 | 70 | 70 | 1:1 | Not Good | Not Good | — | Good |
| Example 8 | 20,000 | 70 | 20 | 2:1 | Not Good | Not Good | — | Good |
| Example 27 | 20,000 | 80 | 80 | 2:1 | Not Good | Not Good | Good | Good |
| Example 25 | 50,000 | 70 | 10 | 2:1 | Not Good | Not Good | Good | Good |
| Example 26 | 50,000 | 70 | 80 | 2:1 | Not Good | Not Good | Good | Good |
| Comparative Example 1 | GRF | N/A | N/A | N/A | Not Good | Not Good | Not Good | Not Good |

TABLE 10

| | | Conditions | | | Biocompatibility |
|---|---|---|---|---|---|
| | Mw | Conc. (%) | 10% chol Gelatin content (wt %) | Succinimidyl group:Amino group | NFκB-RE Expression level (×10⁶ photon/sec) |
| Example 5 | 20,000 | 70 | 70 | 1:1 | 300.77 |
| Example 8 | 20,000 | 70 | 20 | 2:1 | 282.17 |
| Comparative Example 1 | N/A | N/A | N/A | N/A | 516.3 |

As shown in Tables 1 to 8, the adhesive strength of the tissue adhesives of Examples 1 to 27 was higher than the adhesive strength of the tissue adhesive of Comparative Example 1. Moreover, as shown in Table 9, the biocompatibility (degradability) of the tissue adhesives of Examples 2, 5, 8, 27, 25, and 26 was higher than the biocompatibility of the tissue adhesive of Comparative Example 1. Moreover, as shown in Table 10, the inflammation-inducibility of the tissue adhesives of Examples 5 and 8 was lower than the inflammation-inducibility of the tissue adhesive of Comparative Example 1, meaning that the biocompatibility of Examples 5 and 8 was high.

Example 28

Adhesion test of hydrophobically-modified gelatin-DST adhesive with use of porcine vascular membrane
(Experimental Method)

Porcine vascular membrane were exposed and cut out in a size of 1 cm×3 cm for use as a test specimen. Hydrophobically-modified gelatin of a molecular weight of 20,000 was prepared at 70 w/v % with 0.1 M PBS of pH 6 and kept at 37° C. This was added with a disuccinimidyl tartrate (DST) powder which had been weighed so that the amino group: DST succinimidyl group ratio in the gelatin would be 1:1. The mixture was stirred by a pencil mixer for 5 seconds, and immediately applied to the test specimen that had been masked with a silicone sheet having been cut in a size of 1 cm×1 cm and a thickness of 0.5 mm. This was incubated at 37° C. for 10 minutes, and soon measured for the adhesive strength.

(Results and Discussion)

Figure 4:
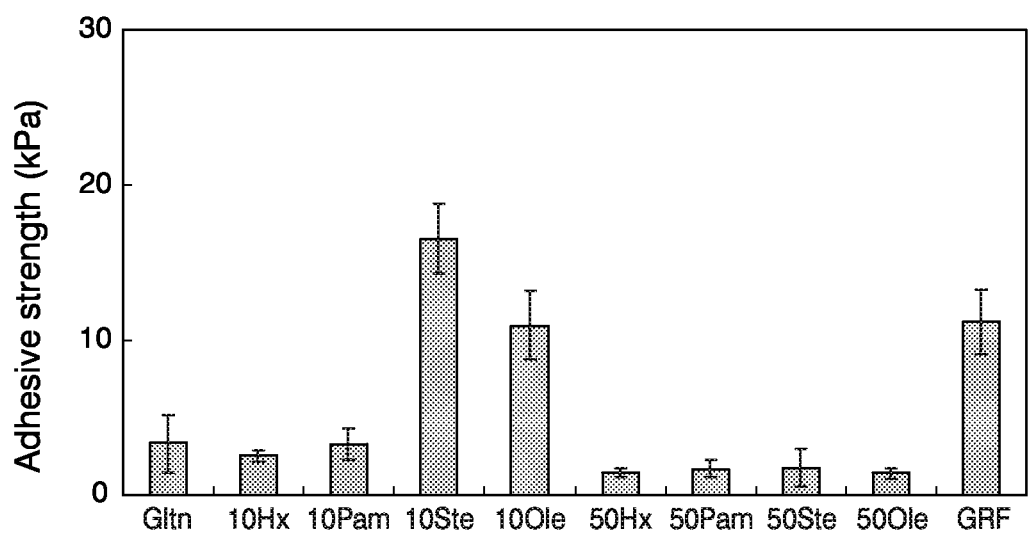
FIG. 4 is a graph showing the results of the adhesion test of hydrophobically-modified gelatin-DST adhesive using porcine vascular media.
Figure 5:
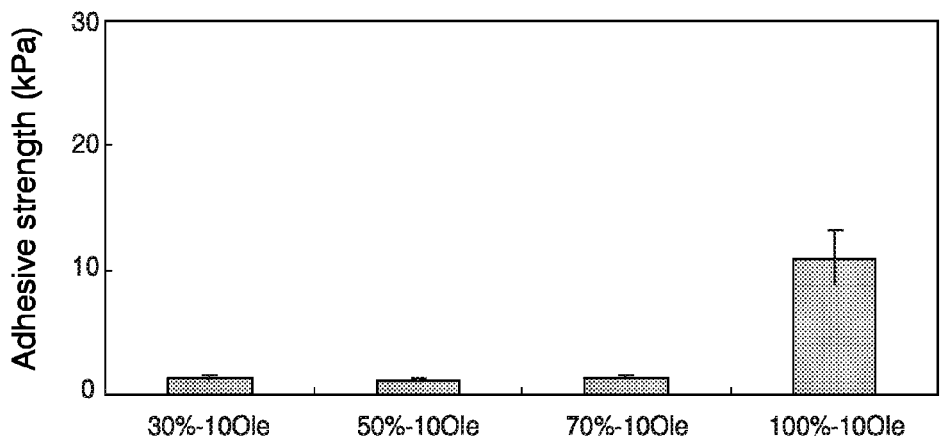
FIG. 5 is a graph showing the results of the adhesion test of hydrophobically-modified gelatin-DST adhesive using porcine vascular media.
Figure 6:
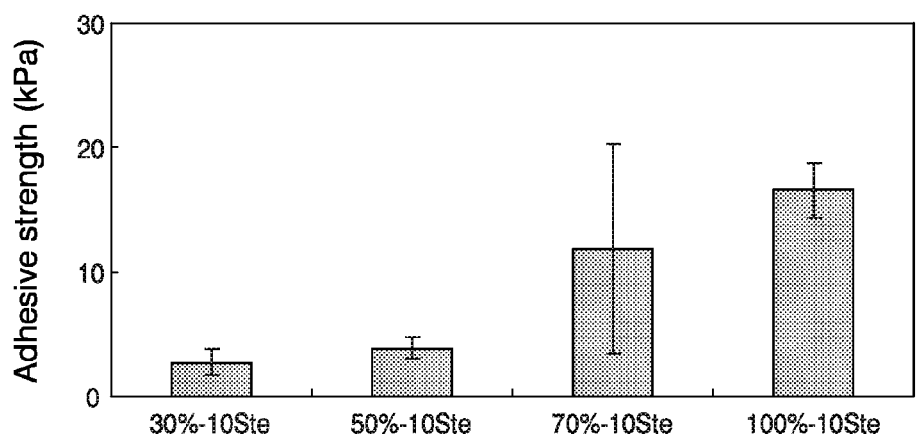
FIG. 6 is a graph showing the results of the adhesion test of hydrophobically-modified gelatin-DST adhesive using porcine vascular media.

The results of the shear test are shown in FIG. 4 to FIG. 6.

In FIG. 4, the symbol Hx means the hexanoyl group, the symbol Pam means the palmitoyl group, the symbol Ste means the stearyl group, and the symbol Ole means the oleyl group. Moreover, the symbols 10Hx, 10OPam, 10Ste, and 10Ole respectively mean that the introduction rate of the hydrophobic group with respect to the amino groups in the gelatin is 10%. Furthermore, the symbols 50Hx, 50OPam, 50Ste, and 50Ole respectively mean that the introduction rate of the hydrophobic group with respect to the amino groups in the gelatin is 50%. The symbol GRF means a commercial product of GRF glue, and the symbol Gltn means untreated gelatin.

In FIG. 5, the symbol 30%-10Ole means a mixture of the gelatin having the hydrophobic modification rate of 10% and the untreated gelatin at a rate of 30:70 (w/w). The symbol 50%-10Ole means a mixture of the gelatin having the hydrophobic modification rate of 10% and the untreated gelatin at a rate of 50:50 (w/w). The symbol 70%-10Ole means a mixture of the gelatin having the hydrophobic modification rate of 10% and the untreated gelatin at a rate of 70:30 (w/w). The 100%-10Ole means the gelatin having the hydrophobic modification rate of 10%.

In FIG. 6, the symbol 30%-10Ste means a mixture of the gelatin having the hydrophobic modification rate of 10% and the untreated gelatin at a rate of 30:70 (w/w). The symbol 50%-10Ste means a mixture of the gelatin having the hydrophobic modification rate of 10% and the untreated gelatin at a rate of 50:50 (w/w). The symbol 70%-10Ste means a mixture of the gelatin having the hydrophobic modification rate of 10% and the untreated gelatin at a rate of 70:30 (w/w). The symbol 100%-10Ste means the gelatin having the hydrophobic modification rate of 10%.

Effective adhesive strength was confirmed in 20-10Step (stearyl group) and Ole (oleyl group). This can be attributed to high strength of the gel itself and the penetration of the stearoyl group into the test specimen. As the introduction rate of the hydrophobic group became greater, the adhesive strength was weakened.

INDUSTRIAL APPLICABILITY

The two-component tissue adhesive and the method for producing the same of the present invention relate to a tissue adhesive having high adhesive strength and high biocompatibility. Therefore, they are industrially applicable in the industrial fields where a tissue adhesive, a tissue sealant, a hemostatic agent, and the like are required, and such other fields.

The invention claimed is:

1. A two-component tissue adhesive composition consisting of a hydrophobically-modified gelatin comprising at least one hydrophobic cholesteryl group linked to lysine residue side chains of polypeptide of said gelatin; and
   a cross-linking reagent that is disuccinimidyl tartrate; wherein ratio of succinimidyl group within said disuccinimidyl tartrate to amino group of said lysine residue are between 1:1 and 2:1, molecular weight of said gelatin is between 10 KDa and about 20 KDa; and wherein adhesive strength of said composition is at least 50 kPa.

2. The two-component tissue adhesive according to claim 1, wherein said first agent further contains gelatin which is any one type or a combination of two or more types selected from the group consisting of natural gelatin derived from human, porcine, bovine, or fish species, and genetically modified gelatin thereof.

* * * * *

UNITED STATES PATENT AND TRADEMARK OFFICE
CERTIFICATE OF CORRECTION

PATENT NO. : 9,499,728 B2
APPLICATION NO. : 13/877880
DATED : November 22, 2016
INVENTOR(S) : Taguchi et al.

It is certified that error appears in the above-identified patent and that said Letters Patent is hereby corrected as shown below:

In the Specification

Column 10, Line 48: now reads "stiffing at 80° C. The mixture was allowed to react by stiffing"
Should read:
-- stirring at 80° C. The mixture was allowed to react by stirring --

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*